(12) United States Patent
Makin et al.

(10) Patent No.: US 7,247,141 B2
(45) Date of Patent: Jul. 24, 2007

(54) INTRA-CAVITARY ULTRASOUND MEDICAL SYSTEM AND METHOD

(75) Inventors: Inder Raj S. Makin, Cincinnati, OH (US); Yoav Avidor, Cincinnati, OH (US); Michael H. Slayton, Tempe, AZ (US); Peter G. Barthe, Phoenix, AZ (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 418 days.

(21) Appl. No.: 10/795,680

(22) Filed: Mar. 8, 2004

(65) Prior Publication Data

US 2005/0197577 A1    Sep. 8, 2005

(51) Int. Cl.
*A61B 8/00* (2006.01)

(52) U.S. Cl. ............ 600/439; 600/437; 600/462; 600/438; 600/459; 601/463; 601/466; 601/471; 601/2; 601/4

(58) Field of Classification Search ........ 600/437–491; 604/19, 20–22; 601/2–4
See application file for complete search history.

(56) References Cited

U.S. PATENT DOCUMENTS

| 4,757,820 A | 7/1988 | Itoh |
| 4,798,215 A | 1/1989 | Turner |
| 4,937,767 A | 6/1990 | Reuschel et al. |
| 5,295,484 A | 3/1994 | Marcus et al. |
| 5,391,197 A | 2/1995 | Burdette et al. |
| 5,465,724 A * | 11/1995 | Sliwa et al. ............ 600/459 |
| 5,485,839 A | 1/1996 | Aida et al. |
| 5,514,085 A * | 5/1996 | Yoon ............ 604/11 |
| 5,547,459 A | 8/1996 | Kaufman et al. |
| 5,549,638 A | 8/1996 | Burdette |
| 5,558,092 A | 9/1996 | Unger et al. |
| 5,571,088 A | 11/1996 | Lennox et al. |
| 5,575,288 A * | 11/1996 | Sliwa et al. ............ 600/445 |
| 5,588,432 A | 12/1996 | Crowley |
| 5,620,479 A | 4/1997 | Diederich |
| 5,657,760 A | 8/1997 | Ying et al. |
| 5,728,062 A | 3/1998 | Brisken |
| 5,733,315 A | 3/1998 | Burdette et al. |
| 5,735,280 A | 4/1998 | Sherman et al. |
| 5,759,154 A | 6/1998 | Hoyns |
| 5,771,896 A * | 6/1998 | Sliwa et al. ............ 600/462 |
| 5,800,379 A | 9/1998 | Edwards |
| 5,860,974 A | 1/1999 | Abele |
| 6,001,069 A | 12/1999 | Tachibana et al. |

(Continued)

*Primary Examiner*—Brian L. Casler
*Assistant Examiner*—Sanjay Cattungal
(74) *Attorney, Agent, or Firm*—Thompson Hine LLP

(57) ABSTRACT

A method for medically employing ultrasound within a body cavity of a patient. An end effector is obtained having a medical ultrasound transducer assembly. A biocompatible hygroscopic substance is obtained having a non-expanded anhydrous state and having an expanded and fluidly-loculated hydrated state. The end effector, including the transducer assembly, and the substance in substantially its anhydrous state are inserted into a body cavity (such as endoscopically inserted into a uterus) of a patient. The transducer assembly is used to medically image and/or medically treat patient tissue (such as stopping blood flow to, and/or ablating, a uterine fibroid). A system for medically employing ultrasound includes the end effector and the substance. In another system, the end effector includes the substance. The substance in its hydrated state expands inside the body cavity providing acoustic coupling between the wall of the body cavity and the transducer assembly.

20 Claims, 3 Drawing Sheets

U.S. PATENT DOCUMENTS

| | | |
|---|---|---|
| 6,004,269 A | 12/1999 | Crowley et al. |
| 6,007,499 A | 12/1999 | Martin et al. |
| 6,135,963 A | 10/2000 | Haider |
| 6,135,971 A | 10/2000 | Hutchinson et al. |
| 6,138,513 A | 10/2000 | Barabash et al. |
| 6,216,704 B1 | 4/2001 | Ingle et al. |
| 6,231,834 B1 | 5/2001 | Unger et al. |
| 6,361,531 B1 | 3/2002 | Hissong |
| 6,521,211 B1 * | 2/2003 | Unger et al. ............... 424/9.52 |
| 6,546,934 B1 | 4/2003 | Ingle et al. |
| 6,575,956 B1 | 6/2003 | Brisken et al. |
| 6,599,245 B1 | 7/2003 | Ma et al. |
| 6,602,251 B2 * | 8/2003 | Burbank et al. ............... 606/45 |
| 6,613,004 B1 | 9/2003 | Vitek et al. |
| 6,618,620 B1 | 9/2003 | Freundlich et al. |
| 6,645,202 B1 | 11/2003 | Pless et al. |
| 6,669,638 B1 | 12/2003 | Miller et al. |
| 6,719,694 B2 | 4/2004 | Weng et al. |
| 6,764,488 B1 * | 7/2004 | Burbank et al. ............... 606/51 |
| 6,921,371 B2 | 7/2005 | Wilson |
| 6,936,024 B1 * | 8/2005 | Houser ......................... 604/22 |
| 6,936,048 B2 * | 8/2005 | Hurst ........................... 606/41 |
| 6,974,417 B2 | 12/2005 | Lockwood et al. |
| 7,037,306 B2 | 5/2006 | Podany et al. |
| 7,078,015 B2 * | 7/2006 | Unger ......................... 424/9.52 |
| 2001/0007940 A1 * | 7/2001 | Tu et al. ....................... 606/41 |
| 2003/0018266 A1 | 1/2003 | Makin et al. |
| 2003/0220568 A1 | 11/2003 | Hansmann et al. |
| 2005/0137520 A1 | 6/2005 | Rule et al. |
| 2006/0052701 A1 * | 3/2006 | Carter et al. ................. 600/439 |

* cited by examiner

INTRA-CAVITARY ULTRASOUND MEDICAL SYSTEM AND METHOD

FIELD OF THE INVENTION

The present invention is related generally to ultrasound, and more particularly to a medical system and method employing ultrasound within a body cavity of a patient.

BACKGROUND OF THE INVENTION

Known ultrasound medical methods include using ultrasound imaging (at low power) of patients to identify patient tissue for medical treatment and include using ultrasound (at high power) to ablate identified patient tissue by heating the tissue. Known ultrasound imaging includes Doppler ultrasound imaging to detect blood flow, and a proposed known use of ultrasound includes using an ultrasound transducer outside the body to stop internal bleeding (by sealing ruptured blood vessels) of a patient brought to an emergency room of a hospital.

In one known ultrasound uterine medical treatment method, an ultrasound transducer is endoscopically inserted into the vagina but outside the uterus of a female patient and is used to ablate a portion of a uterine fibroid. A known method for providing acoustic coupling between the ultrasound transducer and nearby surrounding patient tissue within a body cavity includes surrounding the ultrasound transducer with an expandable outer balloon (i.e., bladder) as part of the ultrasound transducer assembly and injecting water between the ultrasound transducer and the balloon to expand the balloon against some of the body cavity, wherein the water provides the acoustic coupling between the ultrasound transducer and the nearby surrounding patient tissue in contact with the balloon. In another known method, added water is used between the ultrasound transducer and a non-expandable outer sheath of the ultrasound transducer assembly which surrounds the ultrasound transducer, wherein the sheath contacts some of the nearby surrounding patient tissue. In a further known method, added water is used without the balloon or sheath to provide the acoustic coupling. Balloons and sheaths do not contact all of the nearby surrounding patient tissue, especially when the body cavity has sharp body contours, and it is difficult to keep water within the body cavity without the use of a balloon or sheath.

In known non-ultrasound uterine medical treatment methods, blood flow in a uterine artery (or a branch thereof) is blocked by embolization using small micropellets, by ligation, or by fulguration. The aim of such uterine artery blockage is to reduce the size of a uterine fibroid supplied by blood from the uterine artery and/or to reduce abnormal uterine bleeding from such uterine fibroid. Normal uterine tissue is essentially unaffected by these procedures as the uterus is supplied abundant collateral blood via the ovarian arteries. However, having micropellets in an artery can pose potential medical problems, and ligating and fulgurating an artery are relatively invasive procedures.

Known ultrasound medical systems and methods include endoscopically inserting an end effector having an ultrasound transducer transrectally or transurethrally in male patients to medically destroy prostate tissue for benign and cancerous conditions. Rotatable ultrasonic end effectors are known which have an ultrasound imaging transducer on one side and an ultrasonic treatment transducer on the opposite side and which have an ultrasonic treatment transducer of a short focal length on one side and an ultrasonic treatment transducer of a long focal length on the other side. A known ultrasonic end effector also includes a biopsy tool. Known methods for guiding an end effector within a patient include guiding the end effector from x-rays, from MRI images, and from ultrasound images obtained using the ultrasound treatment transducer.

Known non-ultrasound medical systems include endoscopic or laparoscopic clamp end effectors, wherein the clamp end effector is articulated and is steered by the user.

What is needed is an improved medical system and method for employing ultrasound within a body cavity of a patient. This invention addresses those needs lacking in an ultrasonic medical system and/or an ultrasonic medical method.

SUMMARY OF THE INVENTION

A method of the invention is for medically employing ultrasound within a body cavity of a patient and includes steps a) through e). Step a) includes obtaining an end effector having a medical ultrasound transducer assembly. Step b) includes obtaining a biocompatible hygroscopic substance having a non-expanded anhydrous state and having an expanded and fluidly-loculated hydrated state. Step c) includes inserting the end effector including the transducer assembly into the body cavity of the patient. Step d) includes inserting the substance in substantially its anhydrous state into the body cavity. Step e) includes, after steps a) through d), medically imaging and/or medically treating patient tissue with ultrasound from the transducer assembly.

An expression of an embodiment of the invention is for a system for medically employing ultrasound within a body cavity of a patient. The system includes an end effector and a biocompatible hygroscopic substance. The end effector has a medical ultrasound transducer assembly, and the end effector, including the transducer assembly, is insertable into the body cavity of the patient. The substance has a non-expanded anhydrous state and has an expanded and fluidly-loculated hydrated state, wherein the substance is insertable in substantially its anhydrous state into the body cavity. The medical transducer assembly is adapted to medically image and/or medically treat patient tissue with ultrasound.

Another expression of an embodiment of the invention is for a system for medically employing ultrasound within a body cavity of a patient. The system includes an end effector. The end effector includes a medical ultrasound transducer assembly and a biocompatible hygroscopic substance. The end effector including the transducer assembly is insertable into the body cavity of the patient. The transducer assembly includes an ultrasound transducer adapted to medically image and/or medically treat patient tissue. The substance has a non-expanded anhydrous state, has an expanded and fluidly-loculated hydrated state, and is disposed in substantially its anhydrous state on at least a portion of the outside of the transducer assembly.

Several benefits and advantages are obtained from one or more of the method and expressions of the embodiment of the invention. Use of the biocompatible hygroscopic substance provides acoustic coupling between the ultrasound transducer assembly and the wall of the body cavity to medically image and/or treat patient tissue beyond the body cavity without the problems of conventional systems whose balloons and sheaths do not contact all of the nearby surrounding patient tissue (especially when the body cavity has sharp body contours), and whose added water is difficult to keep within the body cavity without the use of such balloons or sheaths.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described embodiments, examples, etc. can be combined with any one or more of the other following-described embodiments, examples, etc.

Figure 1:
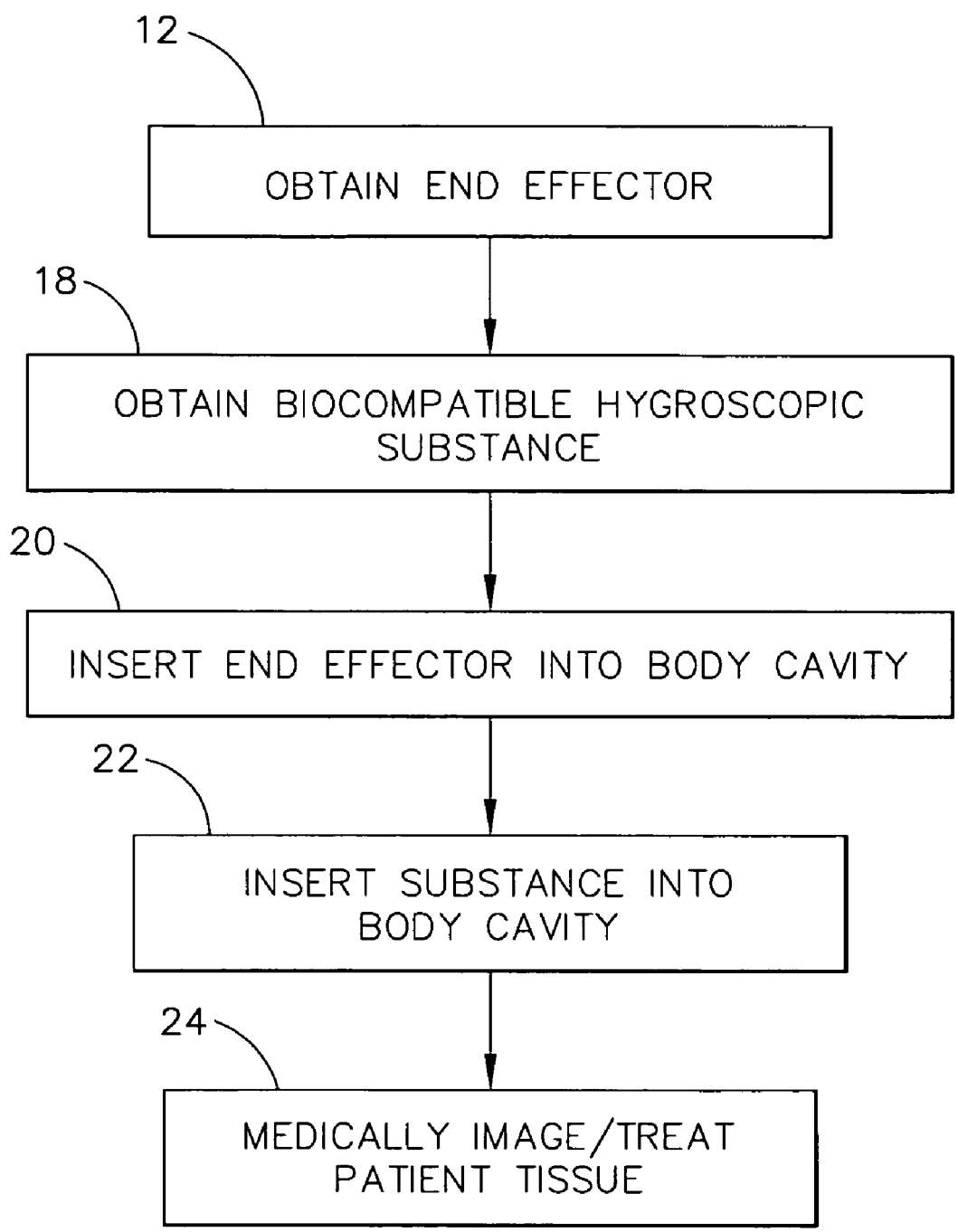
FIG. 1 is a block diagram of a method of the present invention for medically employing ultrasound within a body cavity of a patient.
Figure 2:
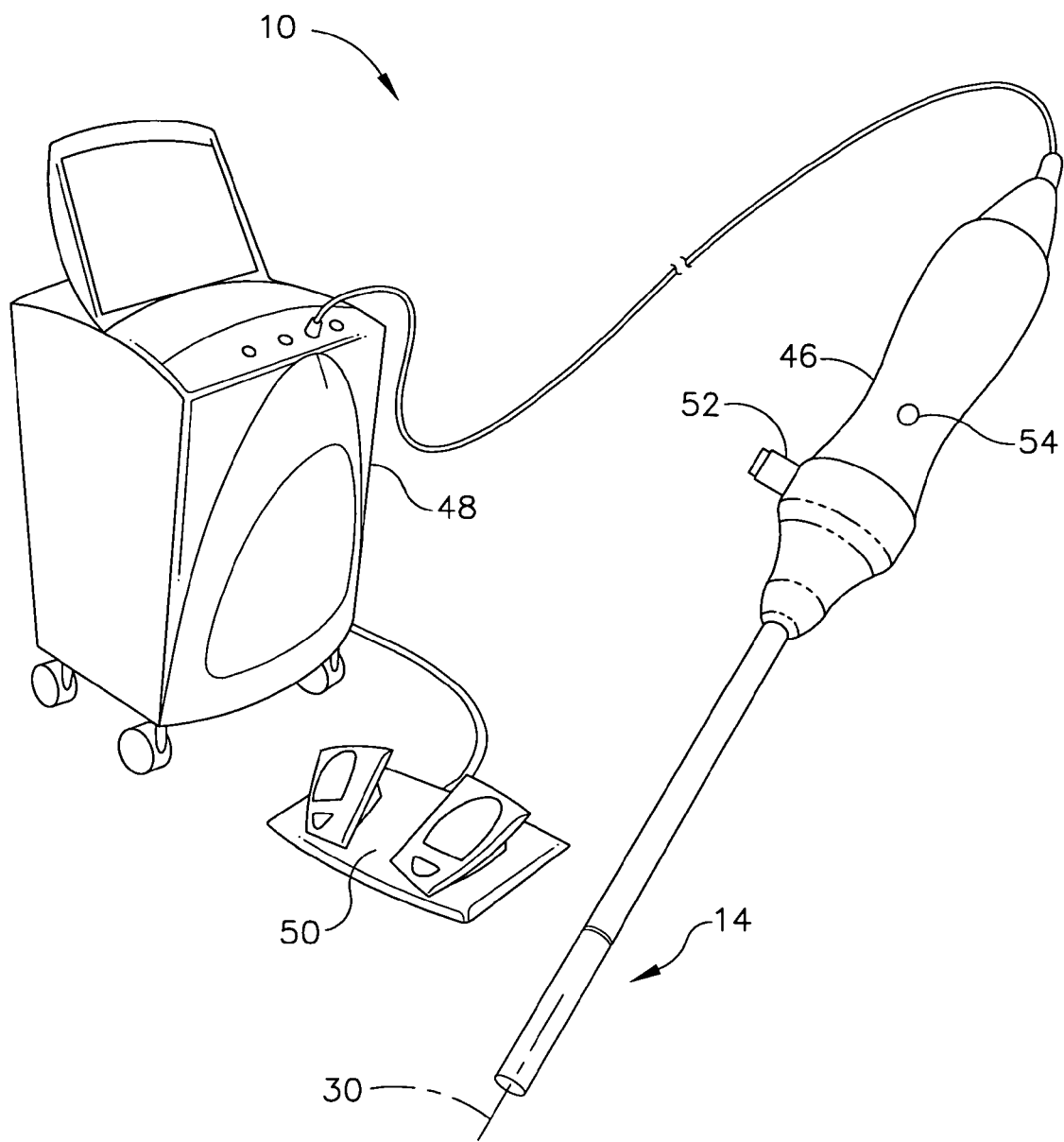
FIG. 2 is a perspective view of an embodiment of a system for medically employing ultrasound within a body cavity of a patient which is used to perform one implementation of the method of FIG. 1.
Figure 3:
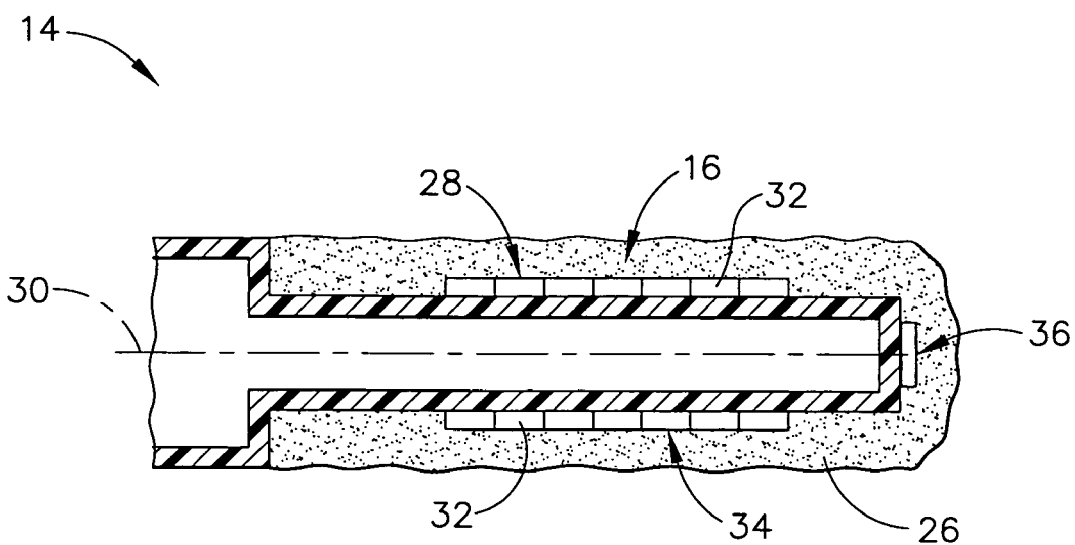
FIG. 3 is a cross-sectional view of the end portion of the end effector of the system of FIG. 2, with wiring omitted for clarity.

Referring now to the Figures, in which like numerals indicate like elements, FIG. 1 illustrates a method of the invention. The method is for medically employing ultrasound within a body cavity of a patient. An embodiment of a system 10 used to perform one implementation of the method of FIG. 1 is shown in FIGS. 2 and 3. The method includes steps a) through e). Step a) is labeled "Obtain End Effector" in block 12 of FIG. 1. Step a) includes obtaining an end effector 14 having an medical ultrasound transducer assembly 16. Step b) is labeled "Obtain Biocompatible Hygroscopic Substance" in block 18 of FIG. 1. Step b) includes obtaining a biocompatible hygroscopic substance having a non-expanded anhydrous state and having an expanded and fluidly-loculated hydrated state. Step c) is labeled "Insert End Effector Into Body Cavity" in block 20 of FIG. 1. Step c) includes inserting the end effector 14 including the transducer assembly 16 into the body cavity of the patient. Step d) is labeled "Insert Substance Into Body Cavity" in block 22 of FIG. 1. Step d) includes inserting the substance in substantially its anhydrous state into the body cavity. Step e) is labeled "Medically Image/Treat Patient Tissue" in block 24 of FIG. 1. Step e) includes, after steps a) through d), medically imaging and/or medically treating patient tissue with ultrasound from the transducer assembly 16.

A medical ultrasound transducer assembly 16 is an apparatus having at least one ultrasound transducer adapted to medically image and/or medically treat a patient such as, but not limited to, a human patient. An ultrasound transducer includes either a single ultrasound transducer element or an array of ultrasound transducer elements, as is known to those skilled in the art. In one embodiment, the medical ultrasound transducer assembly 16 is used in step e) to medically image patient tissue. In another embodiment, the medical ultrasound transducer assembly 16 is used in step e) to medically treat patient tissue. In an a further embodiment, the medical ultrasound transducer assembly 16 is used in step e) to both medically image and medically treat patient tissue.

A biocompatible hygroscopic substance is a substance which will not cause harm to the patient when placed in the body cavity of the patient and which will absorb fluid and/or moisture. A substance having a non-expanded anhydrous state and having an expanded fluidly-loculated hydrated state is a substance which expands to form a fluid-filled loculi structure when in contact with a fluid and/or moisture such as naturally-occuring fluid and/or moisture within the body cavity and/or non-bodily fluid and/or moisture inserted into the body cavity. In one implementation of the method of the invention, the substance comprises polyvinyl alcohol. In one variation, the substance consists essentially of polyvinyl alcohol. It is noted that polyvinyl alcohol in its anhydrous state is a hard solid and in its hydrated state is a gel foam, Other known examples of biocompatible hygroscopic substances which have an expanded fluidly-loculated hydrated state, including those which are a hard solid in their anhydrous state and are a gel foam in their hydrated state are left to the artisan and other presently unknown examples are left to the inventor. However, polyvinyl alcohol is a hygroscopic polymer capable of absorbing large quantities of water and/or moisture, and representative examples of other biocompatible hygroscopic polymers include hydroxy-containing polymers such as partially hydrolzyed polyesters, e.g., partially hydrolzyed acrylate or methacrylate polymers or copolymers, sulfonated polyesters of aromatic dicarboxylic acids and aliphatic or cycloaliphatic glycols including alkali metal derivatives thereof, polyvinlypyrrolidone, polyvinyl imidazol, polyacrylamides, polymethacrylamides, polystyrenesulfonic acid, corn and wheat starch, agar, xanthan gums, gelatin, gelatin derivatives such as phthalated gelatins, cellulose such as hydroxy cellulose, carboxymethyl cellulose and the like, and soluble starches such as dextrin.

In one implementation of the method of the invention, an applicator (not shown) separate from the end effector 14 is used to perform step d). In another implementation, the end effector 14 is used to perform step d). In one methodology, the substance is disposed on the outside of the end effector 14. It is noted that in this methodology, steps c) and d) are performed simultaneously. In one construction, the substance is disposed as a coating on the outside of the end effector 14 with a "corn dog" being a food analogy to the substance-coated end effector. In another methodology, not shown, the substance is deployed into the body cavity from within the end effector 14. Other implementations of step d) are left to the artisan.

In one employment of the method of the invention, after step d), the substance achieves its expanded and fluidly-loculated hydrated state from the natural body fluid and/or moisture present within the body cavity. It is noted that an expanded and fluidly-loculated hydrated state will create a form of the substance which will fill the body cavity, which will conform to the body cavity contour (including sharp contours), and which will provide excellent acoustic coupling between the transducer assembly 16 and the wall of the body cavity. In a different employment, non-bodily fluid and/or moisture, such as sterile water and/or water vapor, is added inside the body cavity to achieve or help achieve the hydrated state of the substance. The term "water" includes "saline solution".

In one deployment of the method of the invention, step c) endoscopically inserts the end effector 14 into the body cavity of the patient, and step d) endoscopically inserts the substance into the body cavity. Other deployments which insert the end effector into a body cavity of the patient include, without limitation, laparoscopic and interstitial insertion of the end effector into a body cavity. In one illustration, the body cavity is the uterus. Other examples of body cavities include, without limitation, the urethra and body cavities of the upper and lower gastrointestinal tract such as the colon.

In a first usage of the method of the invention, step e) medically treats a blood vessel which is a uterine artery or a branch thereof which supplies blood to a portion of the uterus with ultrasound from the transducer assembly 16 to substantially seal the blood vessel to substantially stop the supply of blood to the portion of the uterus from the uterine artery or the branch thereof. In one implementation, there is also included the step of identifying the blood vessel from ultrasound imaging using the transducer assembly 16. It is noted that Doppler ultrasound imaging alone, gray-scale ultrasound imaging alone, and a combination of Doppler and gray-scale ultrasound imaging are known ultrasound techniques to image blood flow in blood vessels. In one variation, the portion of the uterus includes a uterine fibroid. In one modification of the first usage of the method, there is also included the step of medically treating the uterine fibroid with ultrasound from the transducer assembly 16 to ablate at least a part of the uterine fibroid. In one implementation, there is also included the step of identifying the uterine fibroid at least in part from ultrasound imaging using the transducer assembly 16.

In a second usage of the method of the invention, step e) medically treats the endometrium lining of the uterus with ultrasound from the transducer assembly 16 to ablate a desired thickness (or even substantially the entire thickness) of at least a portion of (or even substantially the entire) endometrium lining to substantially stop abnormal uterine bleeding from the endometrium lining. In one implementation, there is also included the step of identifying the endometrium lining of the uterine cavity from ultrasound imaging using the transducer assembly 16. In one extension of the first and/or second usages of the method of the invention, there is also included the step of taking a biopsy of the uterus, wherein the end effector 14 also includes a biopsy tool (not shown). Other usages of the method of the invention are left to the artisan.

After medical imaging and/or treatment, the transducer assembly 16 is withdrawn from the body cavity, and the substance is naturally secreted from the body cavity, and/or is absorbed within patient tissue and later naturally eliminated from the body, and/or is vacuumed from the body cavity by a separate appliance or by a vacuum feature of the end effector 14 (before the end effector 14 is withdrawn from the body cavity), as can be appreciated by those skilled in the art.

An adaptation of the method of the invention is a method for medically employing ultrasound to the exterior of a patient and includes several steps. One step includes obtaining an end effector having a medical ultrasound transducer assembly, and another step includes obtaining a biocompatible hygroscopic substance having a non-expanded anhydrous state and having an expanded and fluidly-loculated hydrated state. A further step includes applying the substance to the exterior of the patient, and an additional step includes disposing the transducer assembly in contact with the substance. A final step includes medically imaging and/or medically treating patient tissue with ultrasound from the transducer assembly. One example of the adapted method includes the step of applying moisture to the substance if moisture on the exterior of the patient is insufficient for the substance to reach its expanded and fluidly-loculated hydrated state.

An embodiment of a system 10 of the invention is for medically employing ultrasound within a body cavity of a patient and is shown in FIGS. 2-3. In a first expression of the embodiment of FIGS. 2-3, the system 10 includes an end effector 14 and a biocompatible hygroscopic substance 26. The end effector 14 has a medical ultrasound transducer assembly 16, and the end effector 14 including the transducer assembly 16 is insertable into the body cavity of the patient. The substance 26 has a non-expanded anhydrous state and has an expanded and fluidly-loculated hydrated state. The substance 26 is insertable in substantially its anhydrous state into the body cavity. The medical transducer assembly 16 is adapted to medically image and/or medically treat patient tissue with ultrasound.

In one choice of materials for the first expression of the embodiment of FIGS. 2-3, the substance 26 comprises polyvinyl alcohol. In one variation, the substance 26 consists essentially of polyvinyl alcohol. As previously noted, polyvinyl alcohol in its anhydrous state is a hard solid and in its hydrated state is a gel foam, Other known examples of such substances 26 which have an expanded fluidly-loculated hydrated state, including those which are a hard solid in their anhydrous state and are a gel foam in their hydrated state are left to the artisan and other presently unknown examples are left to the inventor. However, polyvinyl alcohol is a hygroscopic polymer capable of absorbing large quantities of water and/or moisture and representative examples of hygroscopic polymers are listed in the previous description of the method of the invention. In one arrangement, the end effector 14 is adapted for endoscopic insertion into the body cavity. In one application, the body cavity is the uterus, and the end effector 14 is a rotatable and articulated end effector. In one option, not shown, an applicator separate from the end effector 14 is used to hold the substance 26, wherein the applicator is insertable into the body cavity of the patient.

In a second expression of the embodiment of FIGS. 2-3, the system 10, for medically employing ultrasound within a body cavity of a patient, includes an end effector 14. The end effector 14 includes a medical ultrasound transducer assembly 16 and a biocompatible hygroscopic substance 26. The end effector 14 including the transducer assembly 16 is insertable into the body cavity of the patient. The transducer assembly 16 includes an ultrasound transducer 28 adapted to medically image and/or treat patient tissue. The substance 26 has a non-expanded anhydrous state, has an expanded and fluidly-loculated hydrated state, and is disposed in substantially its anhydrous state on at least a portion of the outside of the transducer assembly 16. It is noted that the term "disposed" includes directly disposed without any intervening apparatus and/or composition and includes indirectly disposed with some intervening apparatus and/or composition, wherein such intervening apparatus and/or composition has been adapted to provide acoustic coupling between the substance 26 and the transducer assembly 16.

In one choice of materials for the second expression of the embodiment of FIGS. 2-3, the substance 26 comprises polyvinyl alcohol. In one variation, the substance 26 consists essentially of polyvinyl alcohol. As previously noted, polyvinyl alcohol in its anhydrous state is a hard solid and in its hydrated state is a gel foam, Other known examples of such substances 26 which have an expanded fluidly-loculated hydrated state are listed in the previous discussion of the method of the invention.

In a first design of the system, shown in FIGS. 2-3, the ultrasound transducer 28 is disposed on the outside of the transducer assembly 16, and the substance 26 in its anhydrous state is disposed (directly or indirectly) on the ultrasound transducer 28. In one arrangement, best seen in FIG. 3, the end effector 14 has a longitudinal axis 30, and the ultrasound transducer 28 is a linear array of longitudinally-disposed and transversely-outwardly-facing ultrasonic transducer elements 32. In this arrangement, the end effector 14 also has an opposing (and in one example substantially identical) ultrasound transducer 34 which is a linear array of longitudinally-disposed and transversely-outwardly-facing ultrasonic transducer elements 32. The end effector 14 further has a longitudinally-facing ultrasonic tip transducer 36. The substance 26 in substantially its anhydrous state is disposed (directly or indirectly) on the outside of the ultrasound transducer 28 such as being attached thereto by a process in which a very limited quantity of water/moisture is added to the substance 26 in its anhydrous state to create a paste consistency followed by surrounding the end effector 14 with the paste followed by drying out the paste resulting in an adhered hard solid coating of the substance 26 on the end effector 14.

In one construction, the end effector 14 is adapted for endoscopic insertion into the body cavity. In one application, the body cavity is the uterus, and the end effector 14 is a rotatable and articulated end effector. In one extension, the end effector 24 also includes a biopsy tool (not shown).

Figure 4:
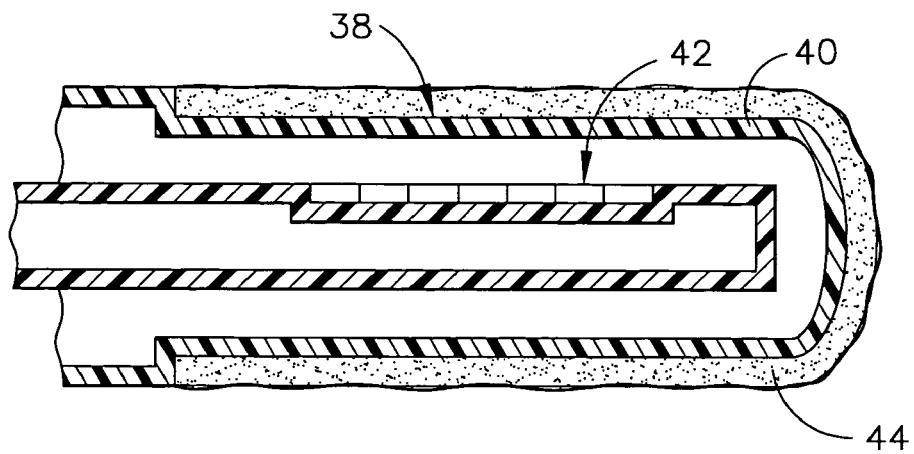
FIG. 4 is a cross-sectional view, as in FIG. 3, but of a different embodiment of the end effector.

An alternate embodiment of a transducer assembly 38 is shown in FIG. 4. Transducer assembly 38 includes a non-expandable sheath 40 (having an acoustic window omitted from FIG. 4 for clarity) surrounding the ultrasound transducer 42 and is adapted for receiving non-bodily fluid (such as sterile water) between the ultrasound transducer 42 and the sheath 40 (for acoustic coupling between the ultrasound transducer 42 and the sheath 40). The substance 44 (which is identical to the previously-described substance 26) in substantially its anhydrous state is disposed (directly or indirectly) on at least a portion of the sheath 40.

In another design, not shown, the substance 26 and 44 is deployed into the body cavity from within the end effector 14.

In one enablement, as shown in FIG. 2, the ultrasound medical treatment system 10 also includes a handpiece 46 which is operatively connected to the end effector 14 and to an ultrasound controller 48, wherein the ultrasound controller 48 is operatively connected to a foot-pedal power switch 50, as can be appreciated by the artisan. In one variation, the handpiece 46 includes a control knob 52 used to articulate the end effector 14 and includes a control button 54 used to rotate the end effector 14, as is within the level of construction skill of the artisan.

It is noted that any of the systems of FIGS. 2-3 and 4 can be adapted for application of the substance 26 and 44 and the transducer assembly 16 and 38 to the exterior of the patient for medically imaging and/or medically treating patient tissue within the patient. In this adaptation, the substance is disposable on the exterior of the patient, and the transducer assembly is disposable to contact the substance. An advantage of this adaptation is the avoidance of "leaky" balloon-based coupling materials, easy storage and transport, and easy disposal of the substance following the completion of the ultrasound procedure.

Several benefits and advantages are obtained from one or more of the methods and expressions of embodiments of the invention. Use of the biocompatible hygroscopic substance provides acoustic coupling between the ultrasound transducer assembly and the wall of the body cavity to medically image and/or treat patient tissue beyond the body cavity without the problems of conventional systems whose balloons and sheaths do not contact all of the nearby surrounding patient tissue (especially when the body cavity has sharp body contours), and whose added water is difficult to keep within the body cavity without the use of such balloons or sheaths.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the device and method of the present invention has been illustrated in relation to (e.g. resection), but it will be understood the present invention has applicability. Moreover, the structure of each element associated with the present invention can be alternatively described as a means for providing the function performed by the element. It will be understood that the foregoing description is provided by way of example, and that other modifications may occur to those skilled in the art without departing from the scope and spirit of the appended claims.

What is claimed is:

1. A method for medically employing ultrasound within a body cavity of a patient comprising the steps of:
   a) obtaining an end effector having a medical ultrasound transducer assembly;
   b) obtaining a biocompatible hygroscopic substance having a non-expanded anhydrous state and having an expanded and fluidly-loculated hydrated state;
   c) inserting the end effector including the transducer assembly into the body cavity of the patient;
   d) inserting the substance in substantially its anhydrous state into the body cavity;
   e) after steps a) through d), medically imaging and/or medically treating patient tissue with ultrasound from the transducer assembly; and
   f) after step e) allowing the substance to remain in the body cavity for at least one of natural secretion and absorption followed by natural elimination and vacuuming the substance from the body cavity.

2. The method of claim 1, wherein the substance comprises polyvinyl alcohol.

3. The method of claim 2, wherein the substance consists essentially of polyvinyl alcohol.

4. The method of claim 1, wherein step c) endoscopically inserts the end effector into the body cavity of the patient, and wherein step d) endoscopically inserts the substance into the body cavity.

5. The method of claim 4, wherein the body cavity is the uterus.

6. The method of claim 5, wherein step e) medically treats a uterine artery or a branch thereof which supplies blood to a portion of the uterus with ultrasound from the transducer assembly to substantially seal the blood vessel to substantially stop the supply of blood to the portion of the uterus from the uterine artery or the branch thereof.

7. The method of claim 6, wherein the portion of the uterus includes a uterine fibroid.

8. The method of claim 7, also including the step of medically treating the uterine fibroid with ultrasound from the transducer assembly to ablate at least a part of the uterine fibroid.

9. The method of claim 5, wherein step e) medically treats the uterine fibroid with ultrasound from the transducer assembly to ablate at least a part of the uterine fibroid.

10. The method of claim 5, wherein step e) medically treats the endometrium lining of the uterus with ultrasound from the transducer assembly to ablate a desired thickness of at least a portion of the endometrium lining to substantially stop abnormal uterine bleeding from the endometrium lining.

11. A system for medically employing ultrasound within a body cavity of a patient comprising:
   a) an end effector having a medical ultrasound transducer assembly, wherein the end effector including the transducer assembly is insertable into the body cavity of the patient; and
   b) a biocompatible hygroscopic substance having a non-expanded anhydrous state and having an expanded and fluidly-loculated hydrated state, wherein the substance is insertable in substantially its anhydrous state into the body cavity;
   wherein the medical transducer assembly is adapted to medically image and/or medically treat patient tissue with ultrasound, and
   wherein the substance is at least one of naturally secretable from the body cavity, absorbable within patient tissue and later naturally eliminatable from the body, and vacuumable from the body cavity.

12. The system of claim 11, wherein the substance comprises polyvinyl alcohol.

13. The system of claim 11, wherein the end effector is adapted for endoscopic insertion into the body cavity.

14. The system of claim 12, wherein the body cavity is the uterus, and wherein the end effector is a rotatable and articulated end effector.

15. A system for medically employing ultrasound within a body cavity of a patient comprising an end effector, wherein the end effector includes a medical ultrasound transducer assembly and a biocompatible hygroscopic substance, wherein the end effector including the transducer assembly is insertable into the body cavity of the patient, wherein the transducer assembly includes an ultrasound transducer adapted to medically image and/or medically treat patient tissue, wherein the substance has a non-expanded anhydrous state, has an expanded and fluidly-loculated hydrated state, and is disposed in substantially its anhydrous state on at least a portion of the outside of the transducer assembly, and wherein the substance is at least one of naturally secretable from the body cavity, absorbable within patient tissue and later naturally eliminatable from the body, and vacuumable from the body cavity.

16. The system of claim 15, wherein the substance comprises polyvinyl alcohol.

17. The system of claim 15, wherein the ultrasound transducer is disposed on the outside of the transducer assembly, and wherein the substance in substantially its anhydrous state is disposed on the ultrasound transducer.

18. The system of claim 15, wherein the transducer assembly includes a non-expandable sheath surrounding the ultrasound transducer and is adapted for receiving non-bodily fluid between the ultrasound transducer and the sheath, and wherein the substance in substantially its anhydrous state is disposed on at least a portion of the sheath.

19. The system of claim 15, wherein the end effector is adapted for endoscopic insertion into the body cavity.

20. The system of claim 19, wherein the body cavity is the uterus, and wherein the end effector is a rotatable and articulated end effector.

* * * * *